United States Patent [19]

Asakura et al.

[11] Patent Number: 4,767,520

[45] Date of Patent: Aug. 30, 1988

[54] DEVICE FOR DETECTING AIR-FUEL RATIO OF ENGINE

[75] Inventors: Masahiko Asakura, Saitama; Tomohiko Kawanabe, Tochigi; Noritaka Kushida, Tokyo, both of Japan

[73] Assignee: Honda Giken Kogyo Kabushiki Kaisha, Tokyo, Japan

[21] Appl. No.: 865,556

[22] Filed: May 21, 1986

[30] Foreign Application Priority Data

May 27, 1985 [JP] Japan ................................ 60-113406

[51] Int. Cl.[4] ............................................. G01N 27/58
[52] U.S. Cl. ..................................... 204/406; 204/412; 204/425; 123/440; 123/489
[58] Field of Search ................ 123/440, 489; 204/412, 204/421, 425, 431, 406

[56] References Cited

U.S. PATENT DOCUMENTS

| 4,440,621 | 4/1984 | Kitahara et al. | 204/406 |
| 4,534,330 | 8/1985 | Osuga et al. | 123/440 |
| 4,601,273 | 7/1986 | Kitahara et al. | 123/440 |
| 4,601,276 | 7/1986 | Danson et al. | 123/489 |
| 4,609,453 | 9/1986 | Shimomura | 204/425 |
| 4,658,790 | 4/1987 | Kitahara | 204/425 |

Primary Examiner—John F. Niebling
Assistant Examiner—Ben C. Hsing
Attorney, Agent, or Firm—Lyon & Lyon

[57] ABSTRACT

A device for detecting the air-fuel ratio of an engine by measuring the oxygen concentration of the exhaust gas by means of an oxygen sensor including an oxygen pump and a cell element for measuring the oxygen concentration ratio, comprising a filter circuit for smoothing the output signal of the oxygen sensor, said filter circuit having a time constant which is variably set so that it is in proportional relation to the number of revolutions per units of time of the engine.

2 Claims, 3 Drawing Sheets

DEVICE FOR DETECTING AIR-FUEL RATIO OF ENGINE

BACKGROUND OF THE INVENTION

1. Field of the Invention

The present invention relates to a device for detecting air-fuel ratio of an engine in which an oxygen sensor of oxygen-concentration proportional type is used.

2. Prior Art

A prior art system of this kind is shown in FIG. 4. Use is made of an oxygen sensor of the oxygen-concentration proportional type which includes oxygen-ion conductive and solid electrolyte materials 1 and 2, a spacer 3 made of inorganic heat-resistant adhesive material interposed between said electrolyte materials to partly form restricted region, such as a gap G, therebetween and a pair of opposing electrodes 4 and 5 arranged at the positions of said gap G, respectively, one of which constitutes an oxygen pump element 6 and the other of which constitutes a cell element 7 for measuring an oxygen concentration ratio. The air-fuel ratio of the engine is detected by measuring the oxygen concentration in the exhaust gas, for example.

Such oxygen sensor is positioned in the exhaust gas pipe and a D.C. voltage $V_B$ is applied between the electrodes 4 at the side of the oxygen pump element 6, with the polarity as shown in the drawing. Then, the oxygen ion passes through the solid electrolyte material 1 of the oxygen pump element 6 and the oxygen in the gap G leaks through said material to the outside. Accordingly, a difference in oxygen concentration between the gap G and the outside is produced so that an electromotive force E is generated by the cell element 7. At this time the electromotive force E produced by the cell element 7 is compared with a reference voltage by means of a comparator CMP and the pump current Ip fed to the oxygen pump element 6 is subjected to feed-back control so that $E=Vs$. Thus the oxygen concentration in the exhaust gas is obtained, depending upon the value of the pump current Ip which is obtained at this moment with a linear characteristic.

The output signal of the oxygen sensor produced at this time is proportional to the air-fuel ratio of the engine. For example, it is assumed that the reference voltage Vs is set at 40 mV. Then, if the variation of value of the output voltage converted from the value of the pump current Ip is within the range of 0~1.5 V, it is possible to detect the air-fuel ratio of the engine within the range of 14.6~27 air-fuel ratio.

However, a problem resides in the case of detection of the air-fuel ratio of the engine by means of the oxygen sensor arranged in the exhaust pipe. That is, pulsations arise in the exhaust gas, depending upon the operation of the engine and thus a hunting arises in the output signal of the oxygen sensor (see FIG. 2(a)), so that an error may be produced in the value of the air-fuel ratio of the engine detected on the basis of the output signal of the oxygen sensor. Particularly, in the case of a lean-burn engine, when the air-fuel ratio control is effected to hold the air-fuel ratio of the engine at a predetermined value, in accordance with the output signal of the oxygen sensor, the accuracy of the air-fuel ratio control is considerably reduced, owing to the error of the air-fuel ratio detected by the oxygen sensor having a linear characteristic in the lean area.

OBJECT OF THE INVENTION

In view of the problem as described above, it is an object of the present invention to provide a device for detecting the air-fuel ratio of an engine by measuring the oxygen concentration of an exhaust gas by using an oxygen sensor in which the detection of the air-fuel ratio can be effected always in a stable manner, without being subjected to the influence of the hunting of the output signal of the oxygen sensor which is caused by the pulsation of the exhaust gas.

SUMMARY OF THE INVENTION

In order to attain the object as described above, the present invention provides a device for detecting the air-fuel ratio of an engine which comprises a filter circuit for smoothing the output signal of the oxygen sensor, thereby suppressing the hunting of the output signal of the oxygen sensor.

DESCRIPTION OF THE PREFERRED EMBODIMENT

Now, an embodiment of the present invention will be explained in detail with reference to the drawings.

Figure 1:
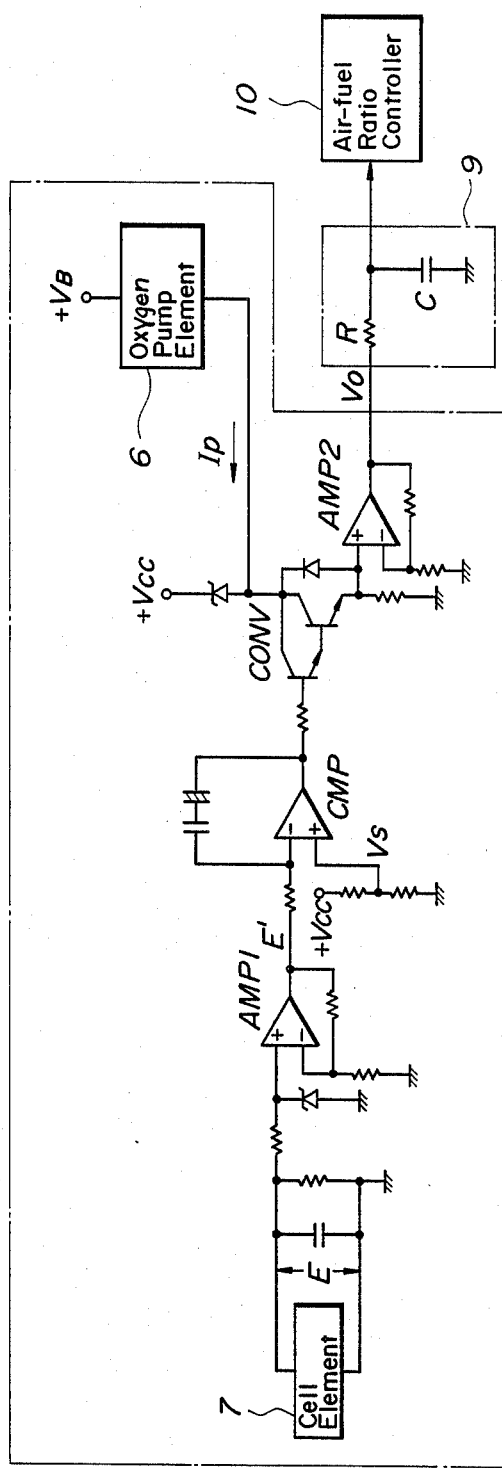
FIG. 1 is an electrical wiring diagram illustrating one embodiment of the device for detecting the air-fuel ratio of an engine according to the present invention.

The device for detecting the air-fuel ratio of an engine, as shown in FIG. 1, comprises an oxygen sensor 8, a filter circuit 9 and an air-fuel ratio controller 10. The filter circuit 9 consists of a resistor R and a capacitor C and serves to smooth the output signal Vo of the oxygen sensor 8.

Figure 2:
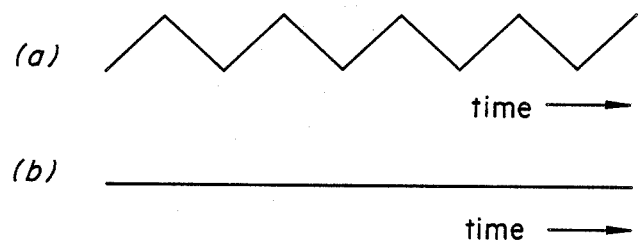
FIG. 2 is a characteristic diagram showing the output signal of the oxygen sensor and the smoothed signal.

The hunting is normally produced in the output voltage Vo of the oxygen sensor 8, as shown in FIG. 2(a), due to the pulsation of the exhaust gas, depending upon the operation of the engine. Such hunting, however, is smoothed by the filter circuit 9, as shown in FIG. 2(b), and thus a substantially constant voltage is obtained at all times of unchanging engine operation, so that the air-fuel ratio can be detected, without producing error.

In the construction as shown in FIG. 1, the oxygen sensor 8 includes a cell element 7, an amplifier AMP 1 for amplifying the induced voltage E, a comparator CMP for comparing the amplified voltage E' with a reference voltage Vs, a voltage-current converter CONV for feeding the pump current Ip to an oxygen pump element 6 in which the pump current Ip is controlled so that $E'=Vs$, and an amplifier AMP 2 for converting the controlled pump current Ip into a voltage signal to produce the output voltage Vo. The detection signal corresponding to the air-fuel ratio of the engine smoothed by the filter circuit 9 is fed to the air-fuel controller 10, for example, which controls the air-fuel ratio to a predetermined value.

In general, as the number of revolutions per unit of time (i.e. rpm) of an engine increases the pulsation of the exhaust gas tends to increase, so that the degree of hunting of the output voltage Vo of the oxygen sensor 8 tends to increase. Accordingly, more precise detection of the air-fuel ratio can be effected if the time constant of the filter circuit 9 is made variable according to the number of revolutions per unit of time of the engine.

Figure 3:
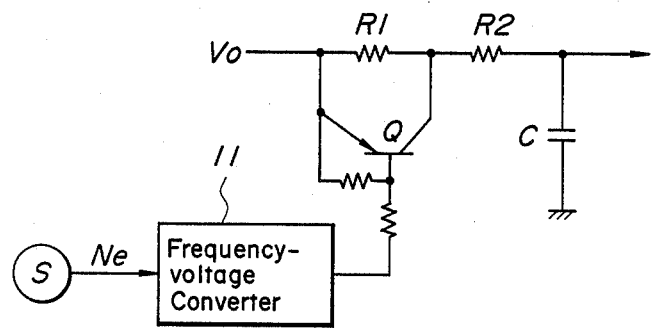
FIG. 3 is an electrical wiring diagram showing a modified construction of the filter circuit.
Figure 4:
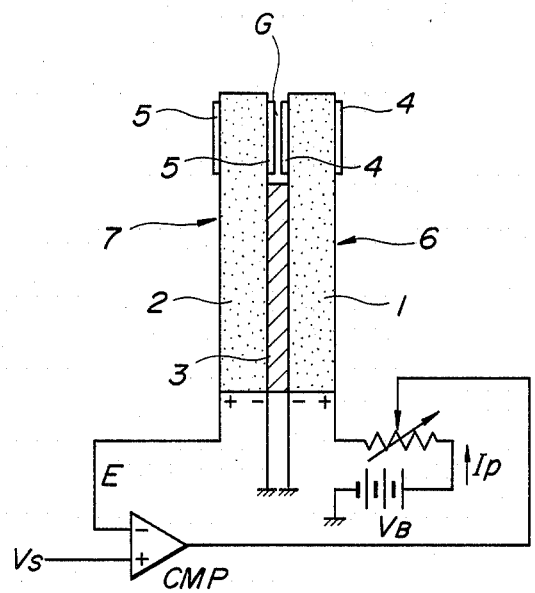
FIG. 4 illustrates the fundamental construction of the conventional oxygen sensor.

A modified form of the filter circuit 9 for smoothing the output voltage Vo of the oxygen sensor 8 is shown in FIG. 3. In the construction as shown in FIG. 3, the RC time constant is made variable according to the number of revolutions per unit of time, i.e. the rotational speed "Ne" of the engine.

In this case, the signal indicating the number of revolutions per unit of time Ne of the engine (pulse signal synchronized with the frequency of revolutions of the engine) which is fed from the revolution sensor S is converted into a voltage signal by means of the frequency-voltage converter 11. If the converted voltage is at a lower level, the transistor Q, which serves as a control switch element, is switched ON, thereby short circuiting the resistor R1 to decrease the RC time constant, and if said voltage is at a higher level, the transistor Q is switched OFF, thereby connecting the resistor R1 into circuit to increase the RC time constant.

In the construction as shown in FIG. 3 the RC time constant of the filter circuit 9 is changed stepwise in accordance with the number of revolutions per unit of time NE of the engine. A modified construction may include a variable resistor in place of the resistor R in the filter circuit 9 and a driver for changing the resistance value of said variable resistor in accordance with the input voltage. In this modified construction the driver is driven by the voltage signal corresponding to the number of revolutions per unit of time NE of the engine, which has been converted by the frequency-voltage converter, and the resistance value is continually changed so that the higher the number of revolutions per unit of time NE is the higher the time constant is and vice versa. Such modified construction enables more precise detection of the air-fuel ratio.

As explained above, the present invention provides a device for detecting an air-fuel ratio of an engine by measuring the oxygen concentration in the exhaust gas by means of the oxygen sensor, which comprises the filter circuit for smoothing the output signal of the oxygen sensor to suppress the hunting of the output signal of the oxygen sensor due to the pulsation of the exhaust gas. Thus, a superior advantage is obtained in that the detection of the air-fuel ratio is effected in a stable manner, without being subjected to the influence of the pulsation of the exhaust gas.

We claim:

1. A device for detecting an air-fuel ratio of an engine by measuring an oxygen concentration of an exhaust gas by means of an oxygen sensor including a pair of oxygen-ion conductive solid electrolyte materials arranged in the gas to be measured, said solid electrolyte materials having electrodes formed on the surfaces thereof and being arranged in confronting relation with each other, with a predetermined restricted region formed therebetween, one of said solid electrolyte materials constituting an oxygen pump element and the other constituting a cell element that develops an electromotive force for measuring an oxygen concentration ratio, said device comprising means for applying a variable electromotive current to the oxygen pump element in response to variations in oxygen concentration for causing the cell element to generate a constant predetermined reference voltage, means for producing an output signal of the oxygen sensor related to the electromotive current applied to the oxygen pump, said output signal being subject to hunting variations in response to pulsations in the exhaust gas, and a filter circuit for receiving and smoothing the output signal of the oxygen sensor for producing the value of the detected air-fuel ratio, said filter circuit having a time constant which is variably set so that it is in proportional relation with respect to the number of revolutions per unit of time of the engine.

2. A device for developing a signal representing oxygen concentration in an exhaust gas of an engine with an oxygen sensor that produces a hunting output signal with continual variations, comprising, an oxygen sensor having an oxygen pump element and a cell element with a restricted region formed therebetween, said elements being of an oxygen-ion conductive solid electrolyte material, means for applying a variable electromotive current to the oxygen pump element in response to variations in oxygen concentration for causing the cell element to generate a constant predetermined reference voltage, means for producing an output signal of the oxygen sensor related to the electromotive current applied to the oxygen pump, said output signal being subject to hunting variations in response to pulsations in the exhaust gas, a filter circuit for receiving and smoothing the hunting output signal, said filter circuit having a variable time constant, and means for varying said filter circuit time constant in proportion to the rotational speed of the engine.

* * * * *